United States Patent
Halalay et al.

(10) Patent No.: US 8,355,880 B2
(45) Date of Patent: Jan. 15, 2013

(54) ON-BOARD METHOD AND SYSTEM FOR MONITORING ONSET OF RAPID OIL OXIDATION AND SLUDGE FORMATION IN ENGINE OILS

(75) Inventors: Ion C. Halalay, Grosse Pointe Park, MI (US); Eric W. Schneider, Shelby Township, MI (US); Robert M. Olree, Troy, MI (US); David R. Staley, Flushing, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 379 days.

(21) Appl. No.: 12/624,654

(22) Filed: Nov. 24, 2009

(65) Prior Publication Data

US 2011/0125425 A1    May 26, 2011

(51) Int. Cl.
*G06F 19/00* (2011.01)
(52) U.S. Cl. .......................................... 702/50
(58) Field of Classification Search ............ 702/50, 702/130, 55, 132, 136
See application file for complete search history.

(56) References Cited

U.S. PATENT DOCUMENTS

| 6,776,024 B2 * | 8/2004 | Jakoby .............................. 73/10 |
| 2008/0027661 A1 * | 1/2008 | Aikawa ............................ 702/50 |
| 2008/0228424 A1 * | 9/2008 | Grosser et al. ................. 702/100 |

OTHER PUBLICATIONS

Solartron 7829 Visconic Industrial Viscosity Transmitter—on line real time viscosity measurement, Emerson Process Management, Sep. 2005, 6 pages.

* cited by examiner

*Primary Examiner* — Edward Raymond
(74) *Attorney, Agent, or Firm* — BrooksGroup

(57) ABSTRACT

In one exemplary embodiment, the state of engine oil degradation is monitored and determined using the size of viscosity hysteresis during heating-cooling cycles. In another exemplary embodiment, the state of engine oil degradation is monitored and determined using the sign of viscosity hysteresis during heating-cooling cycles. In yet another exemplary embodiment, the state of engine oil degradation is monitored and determined using relative viscosity changes hysteresis during heating-cooling cycles.

20 Claims, 3 Drawing Sheets

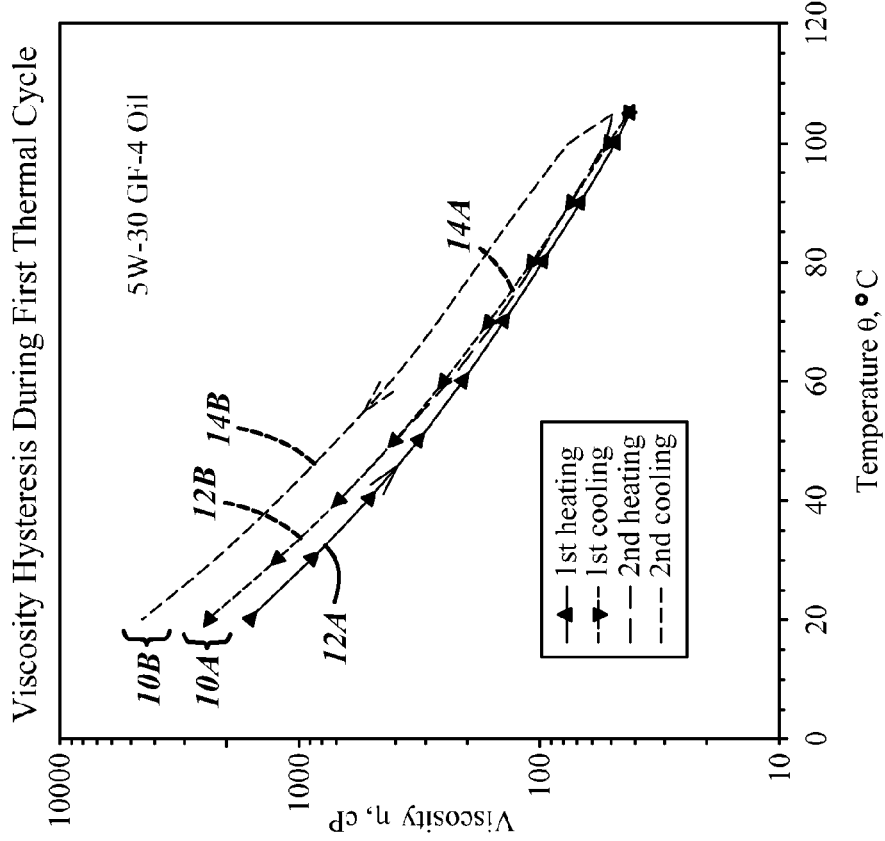
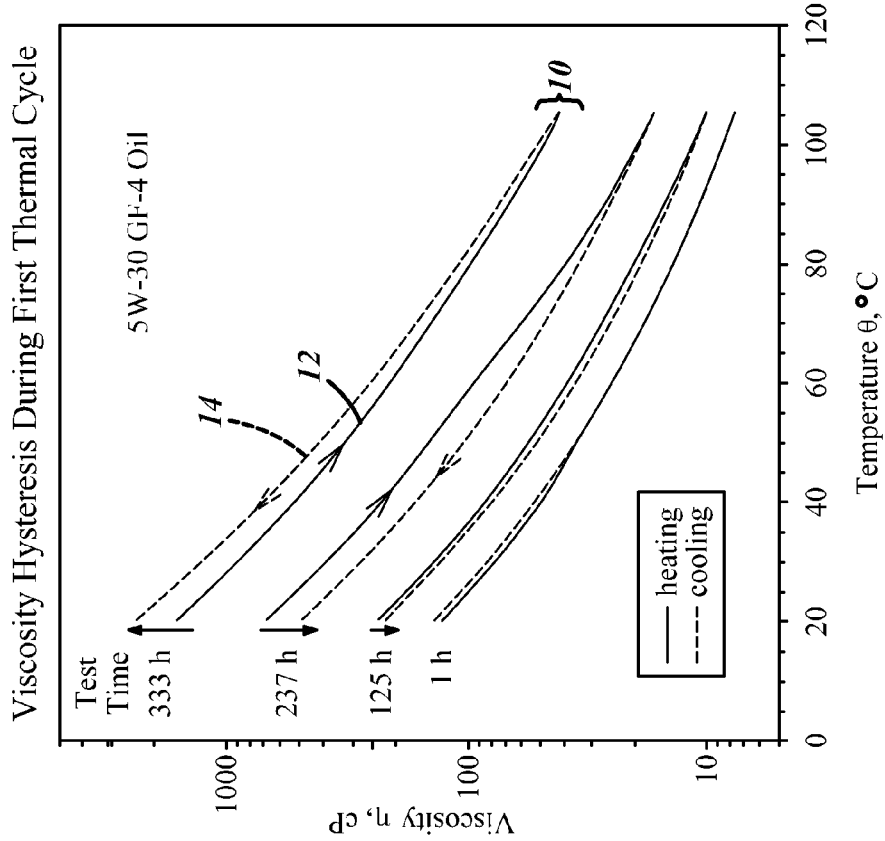
FIG. 2B
FIG. 2A

ON-BOARD METHOD AND SYSTEM FOR MONITORING ONSET OF RAPID OIL OXIDATION AND SLUDGE FORMATION IN ENGINE OILS

TECHNICAL FIELD

The field to which the disclosure relates generally to diagnostic systems and more specifically to an on-board method and system for monitoring engine oils.

BACKGROUND

Engine oils degrade during normal use from a variety of mechanisms. One mode involves oil oxidation and nitration from exposure to oxygen and combustion gases at elevated temperatures in the combustion chamber and the oil sump. Another mode involves contamination of the oil by combustion by-products. The rate of oil degradation may depend on engine operating conditions, ambient temperatures, engine design, and oil quality. If the oil is exposed to engine operating conditions beyond a certain point, a rapid increase in the oil degradation rate may occur, and sludge-forming products may begin to deposit on engine surfaces. The goal of the automotive manufacturer is to maximize the oil change interval for environmental and customer cost/convenience benefits, while ensuring that the oil does not degrade to the point of compromising engine performance or longevity.

One common result of engine oil degradation may be a gradual increase of oil viscosity. The direct measurement of viscosity change may provide a first order estimate of remaining oil life and the onset of rapid degradation. However, viscosity may change for reasons other than oil degradation, such as the top-up addition of oil with a different viscosity grade, or fuel contamination in the oil due to repeated operation at colder temperatures. The on-board measurement of viscosity hysteresis may have the potential to provide a more robust means of determining remaining oil life and of detecting the onset of rapid oil degradation.

Viscosity hysteresis may be experienced by engine oils during thermal cycling, i.e. during heating from a given ambient temperature to an operating temperature, typically in the range of 80 degrees Celsius to 150 degrees Celsius, followed by cooling down to the ambient temperature after engine shut-off. Viscosity hysteresis in engine oil may be a function of the oil's composition and its degree of oxidation during use in an engine. The absolute value of the hysteresis may depend on the degree of oil degradation, wherein the higher absolute value may be an indication of an increase in oil degradation. A change in sign of the hysteresis from negative to positive may also signal the moment when the oil degradation reaches the point when formation of varnish and sludge precursors begins.

SUMMARY OF EXEMPLARY EMBODIMENTS OF THE INVENTION

The exemplary embodiments provide a method and system for monitoring the onset of rapid oil oxidation and sludge formation in engine oils.

In one exemplary embodiment, the onset of rapid oil oxidation and sludge formation in engine oils may be monitored and determined using the sign of viscosity hysteresis during heating-cooling cycles.

In another exemplary embodiment, the onset of rapid oil oxidation and sludge formation in engine oils may be monitored and determined using the size of viscosity hysteresis during heating-cooling cycles.

Other exemplary embodiments of the invention will become apparent from the detailed description provided hereinafter. It should be understood that the detailed description and specific examples, while disclosing exemplary embodiments of the invention, are intended for purposes of illustration only and are not intended to limit the scope of the invention.

BRIEF DESCRIPTION OF THE DRAWINGS

Exemplary embodiments of the invention will become more fully understood from the detailed description and the accompanying drawings, wherein:

FIG. 2A shows viscosity versus temperature graphs recorded during a first thermal cycle for several oil samples collected at various times during an engine dynamometer test, illustrating thermal hysteresis in a mineral-based engine oil;

FIG. 2B illustrates the temperature dependence of the viscosity of the mineral-based engine oil of FIG. 2A in successive thermal cycles for an aliquot collected after 333 test hours.

DETAILED DESCRIPTION OF EXEMPLARY EMBODIMENTS

Figure 1B:
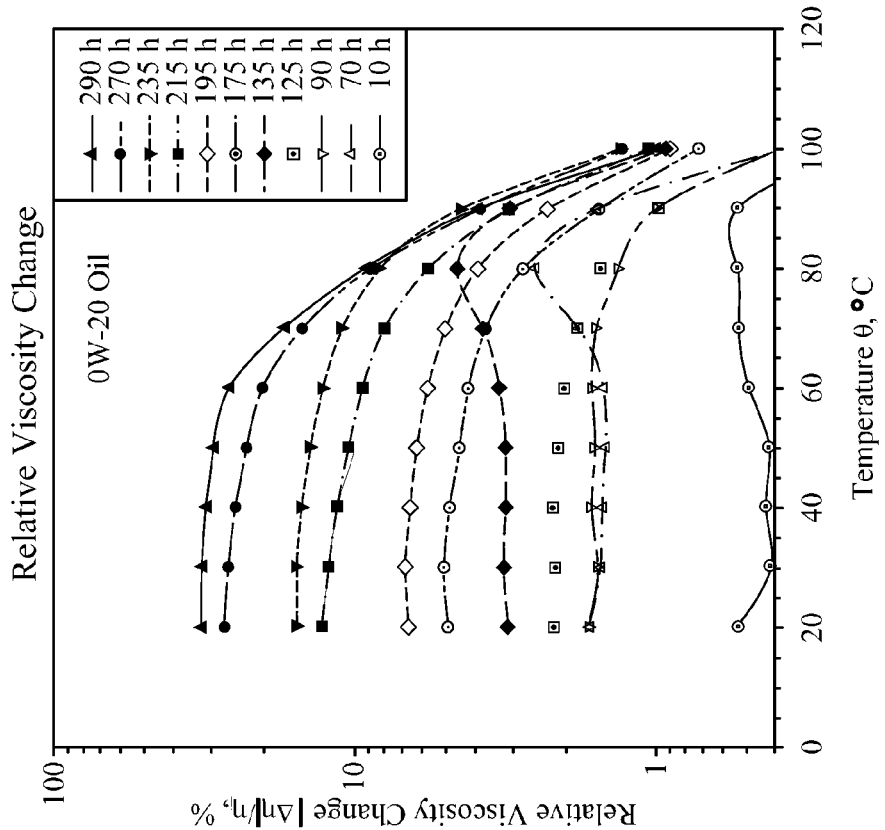
FIG. 1B illustrates the relative viscosity change of the engine oil at various temperatures for the oil samples from FIG. 1A.

The following description of the embodiment(s) is merely exemplary (illustrative) in nature and is in no way intended to limit the invention, its application, or uses.

The exemplary embodiments may provide a method and system for monitoring the onset of rapid oil oxidation and sludge formation in engine oils using viscosity-based engine oil diagnostics.

More specifically, the exemplary embodiments may utilize an on-board method, based on time dependence of the viscosity of an engine oil, to determine the end of useful life of engine oils. This time dependence of viscosity for engine oil may be expressed and measured according to the exemplary embodiments utilizing one or both of two independent viscosity hysteresis phenomena, namely size hysteresis and its sign, which can then be used to predict or calculate the extent of oil degradation and the appearance of sludge precursors.

Hysteresis in a material property generally means the dependence of its values not only on the state of the system, but also on the path of the system in its parameter space, i.e. its previous parameter values and possibly their rates of change. In the present case, the thermal hysteresis in the viscosity of used engine oils means that the measured viscosity values depend not only on the oil temperature, but also whether the measurements were performed during cooling or heating. A viscosity hysteresis graph plots the viscosity of an engine oil as a function of temperature measured when the oil is first heated between predetermined starting and ending temperatures, and then when it is cooled back to the starting temperature to complete a heating-cooling cycle (a.k.a. thermal cycle, as shown in FIGS. 1A, 2A and 2B below). The graphs display the viscosity values measured during heating as solid lines and the viscosity values measured during cooling as dashed lines.

The hysteresis graph may illustrate the size of hysteresis $\Delta\eta(T)$ for a particular heating-cooling cycle 10, which is defined also as the change in viscosity (i.e. $\Delta\eta(T)=\eta_{final}(T)-\eta_{initial}(T)=\eta_{cooling}(T)-\eta_{heating}(T)$) at a particular temperature T between the heating viscosity curve 12 and the cooling viscosity curve 14 in a single heating-cooling cycle.

Moreover, an amplitude of hysteresis (i.e. $|\Delta\eta(T)|$), defined as the absolute value of difference between the viscosity values measured at a given temperature along the entirety of the cooling viscosity curve 14 and heating viscosity curve 12 between the predefined starting and ending temperatures, may also be expressed. A relative hysteresis value (i.e. $|\Delta\eta(T)|/\eta_{heating}$) for a single thermal cycle, defined as the absolute value of difference between the viscosity values measured at a given temperature divided by the "initial" viscosity value, i.e. the viscosity value during heating along the entirety of the cooling viscosity curve 14 and heating viscosity curve 12 between the predefined starting and ending temperatures, can also be used for diagnostic purposes.

In addition, the hysteresis graph may also indicate the sign of hysteresis, whether it be a negative hysteresis or a positive hysteresis, during any heating-cooling cycle 10. A negative hysteresis (i.e. wherein $\Delta\eta(T)=\eta_{cooling}(T)-\eta_{heating}(T)<0$) occurs where the viscosity of the cooling viscosity curve 14 is less than the associated viscosity of the material in the heating viscosity curve 12 for a particular heating-cooling cycle 10 between the predefined starting and ending temperatures, while a positive hysteresis (i.e. wherein $\Delta\eta(T)>0$) occurs where the viscosity of the cooling viscosity curve 14 is greater than the associated viscosity of the material in the heating viscosity curve 12 for a particular heating-cooling cycle 10 between the predefined starting and ending temperatures.

An absolute viscosity change during heating or during cooling in successive thermal cycles (i.e. $\Delta\eta_{heating}(T, N)=\eta_{heating}(T, N)-\eta_{heating}(T, 0)$ or $\Delta\eta_{cooling}(T, N)=\eta_{cooling}(T, N)-\eta_{cooling}(T, 0)$) may also be plotted, which represents the change in viscosity between thermal cycle "N" and an "initial" or "reference" thermal cycle "0," during the heating or during the cooling portion of the thermal cycle, at a particular temperature T as a function of thermal cycle number (i.e. time or number of engine revolutions).

Finally, a relative viscosity change during heating or during cooling for successive thermal cycles (i.e. $\Delta\eta_{heating}(T, N)/\eta_{heating}(T, 0)$ or $\Delta\eta_{cooling}(T, N)/\eta_{cooling}(T, 0)$) may also be plotted which represents the absolute viscosity change divided by an initial viscosity (i.e. measured during the heating or during the cooling portion of an "initial" or "reference" thermal cycle 0) at a particular temperature T as a function of thermal cycle number (i.e. time or number of engine revolutions).

Figure 1A:
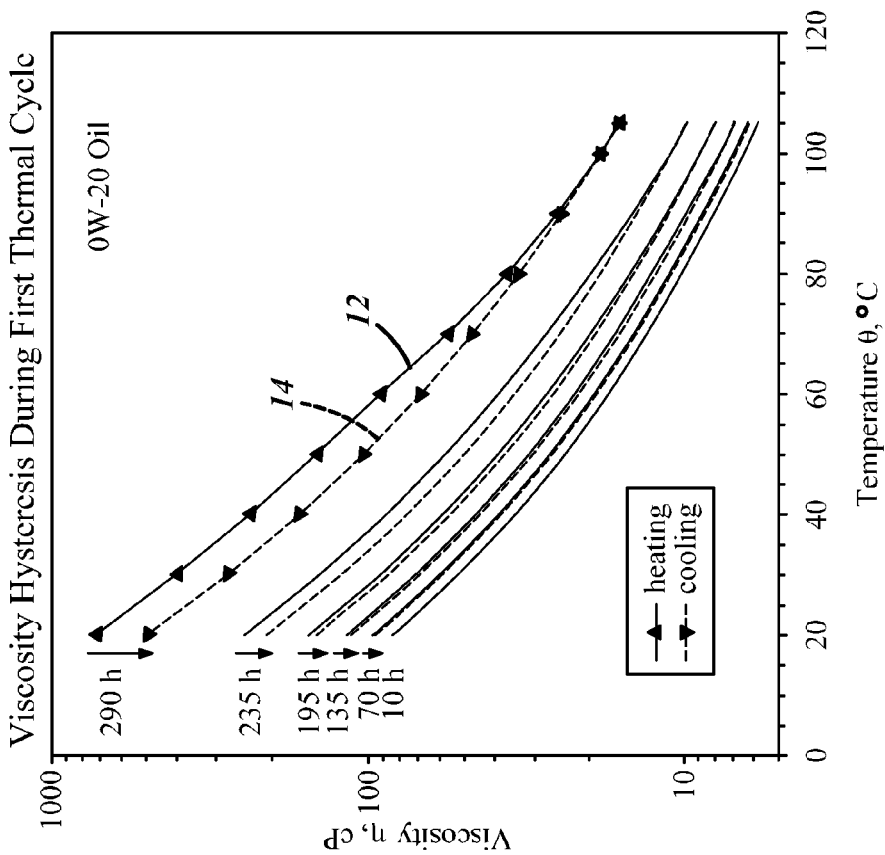
FIG. 1A shows viscosity versus temperature graphs recorded during a first thermal cycle for oil samples collected at various times during an engine dynamometer test, illustrating thermal hysteresis in a synthetic-based engine oil.

Referring first to FIGS. 1A and 1B, an exemplary viscosity hysteresis graph and relative viscosity change graph may be illustrated for synthetic-based engine oils, here a synthetic-based oil with an SAE 0W-20 viscosity rating.

The oil degradation characteristics for known engine oils were evaluated using a high-temperature, high-load (HTHL) dynamometer test. The dynamometer having an engine speed of 3000 rpm, a load of 103 Nm, and an oil sump temperature of about 140 degrees Celsius. Moreover, the viscosity data for FIG. 1A (and FIG. 2A as described below) was measured using a Paar SVM3000 viscometer. In addition, the temperature during the heating cooling-cycle 10 for the oils samples from the dynamometer test described in FIGS. 1A and 2A varied between 20 and 105 degrees Celsius, with an average temperature change rate set at 2 degrees Celsius per minute.

As shown in FIG. 1A, 6 samples of the synthetic SAE 0W-20 oil were taken at pre-determined times (here varying from 10 hours to 290 hours) from an engine dynamometer test under conditions as described above. The engine oil samples were then heated from about 20 degrees Celsius to about 105 degrees Celsius, and then cooled back to about 20 degrees Celsius to complete a thermal cycle 10. The engine oil viscosity was measured continuously during the thermal cycle 10, generating the heating viscosity curve (shown as solid line 12 in FIG. 1A) and cooling viscosity curve (shown as dashed line 14 in FIG. 1A). The thermal cycle 10 is believed to mimic a typical engine performance when an engine is first turned on (generating the heating viscosity curve 12 as the engine warms the oil) and subsequently turned off (generating the cooling viscosity curve 14 wherein the oil cools).

In FIG. 1B, the relative viscosity changes for these 6 samples, as well as other samples collected at varying times during the same dynamometer test, were plotted.

As illustrated in FIG. 1A, the viscosity of the synthetic-based oil degraded over time, as indicated first by an increase in the measured viscosity at the various temperatures along both the heating and cooling curves 12, 14. Moreover, as shown both in FIGS. 1A and 1B, the absolute size of hysteresis, as well as the relative viscosity change, both increased over time. Collectively, these measurements may confirm that the SAE 0W-20 oil degraded over time.

Referring now to FIG. 2A, an exemplary viscosity hysteresis graph (i.e. a hysteresis profile) may similarly be illustrated for mineral-based engine oils, here a commercially available SAE 5W-30 GF-4 oil. In FIG. 2A, four test samples were collected from a dynamometer test under the same test conditions described for FIG. 1A above.

As illustrated in FIG. 2A, the measured viscosity, the absolute amplitude, as well as the size of hysteresis, all increased over time. This test may therefore confirm, similar to FIG. 1A above, that the mineral-based SAE 5W-30 GF-4 engine oil was degrading over time.

Moreover, the sign of hysteresis for the SAE 5W-30 GF-4 mineral-based oil changed from negative (i.e. where the viscosity of the cooling curve is less than the viscosity in the heating curve) to positive at some point between 237 and 333 hours, as expressed on the 333 hour profile. Such a change in the sign of viscosity is believed to occur due to the onset of thermal polymerization of the SAE 5W-30 GF-4 mineral-based engine oil, which correlates with an increase in the amount of oil degradation products that are insoluble in pentane, a phenomenon that is generally associated with the onset of sludge formation.

Referring now to FIG. 2B, a separate (the 333 hours or end-of-test) sample of the mineral-based SAE 5W-30 GF-4 oil was evaluated over two successive thermal cycles 10A and 10B. As the graph illustrates, the viscosities measured along the heating viscosity curve 12B and cooling viscosity curve 14B of the later thermal cycle 10B were greater than the associated viscosities in the first heating viscosity curve 12A and first cooling viscosity curve 12A. Moreover, the size of hysteresis was greater in the later thermal cycle 10B, which is believed to be an indication of an ongoing polymerization reaction.

The exemplary embodiments herein utilize these hysteresis factors as illustrated graphically above in FIGS. 1A, 1B, 2A and 2B to provide an on-board method that may determine the state of oil degradation and the onset of sludge, in order to prevent or minimize deterioration of engine performance. The exemplary embodiments may be utilized in systems having mineral-based or synthetic-based oils. In addition, given the fact that many individuals may introduce additional engine oil to an engine that is not of the same composition as the original oil, the exemplary embodiments may be used for blends of mineral-based oils or synthetic-based oils of varying compositions or states of degradation.

Figure 3:
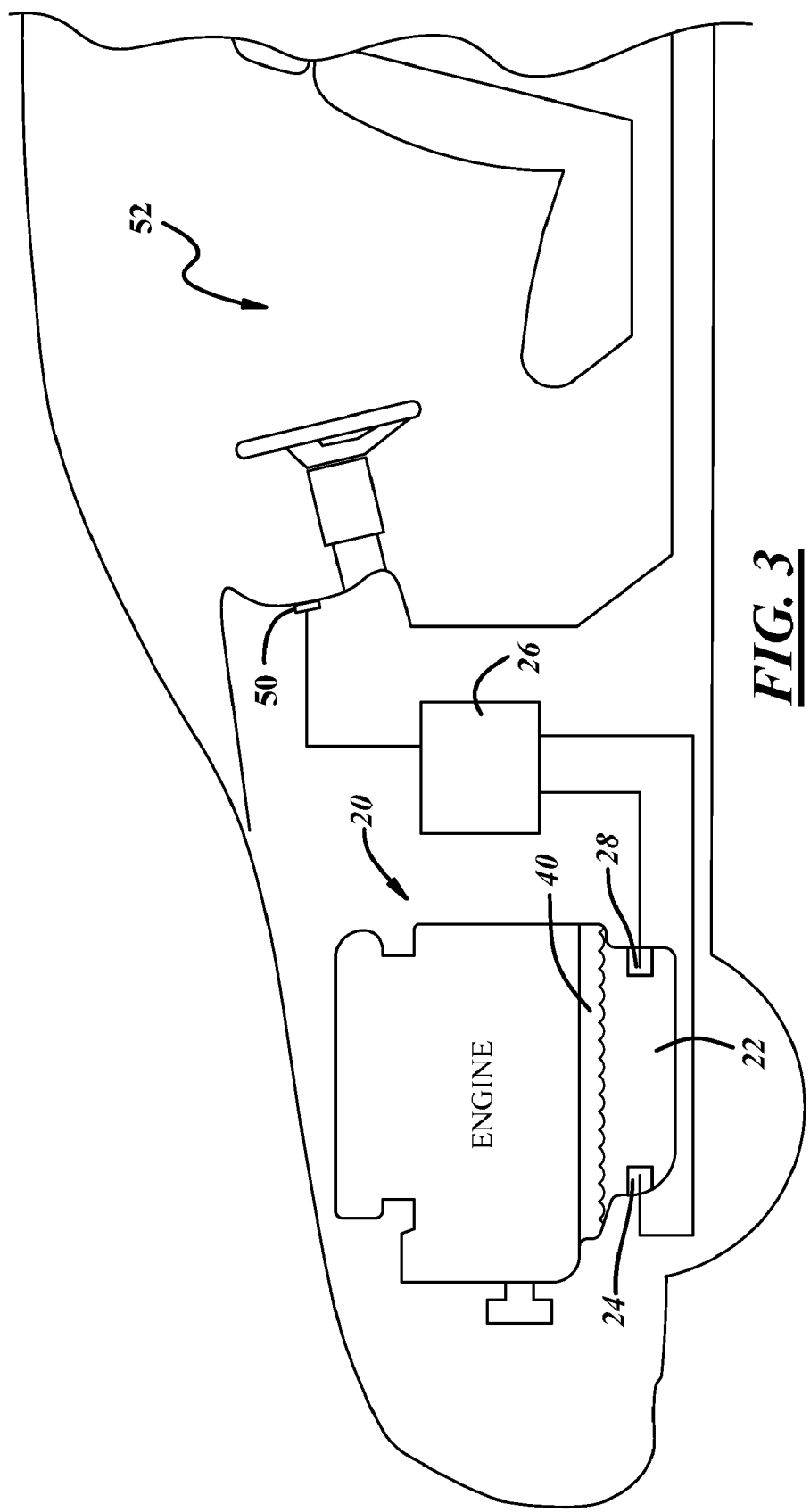
FIG. 3 is a schematic diagram of an automobile including a system for detecting the onset of rapid oil oxidation and sludge formation according to an exemplary embodiment.

In one exemplary method and embodiment, as shown in FIG. 3, an engine 20 having a quantity of engine oil 22 may be provided. The engine oil 22 may be mineral-based or synthetic-based engine oil 22 similar to those described above and illustrated in FIGS. 1A, 1B, 2A and 2B.

One or more sensors 24 may be coupled within the engine 20 at strategic positions within the flow of the engine oil 22. These sensors 24 may be capable of measuring the viscosity of the engine oil 22. One or more temperature sensors 28 may also be provided at strategic positions in the engine 20 to measure the temperature of the engine oil 22. The viscosity sensors 24 and temperature sensors 28 may also be electrically coupled to a processor 26. As shown in FIG. 3, in one example, a single viscosity sensor 24 and a single temperature sensor 28 may be coupled within the oil pan 40 and may be electronically coupled to the processor 26.

Many different types of viscosity sensors 24 that are capable of being electronically coupled to the processer 26 may be utilized individually or in combination in the exemplary embodiments. In various exemplary embodiments, the viscosity sensor 24 may be a torsion-based device (similar to the VISCOLITE 1100LX1 on-line viscometer, available from Hydramotion Ltd. of Malton, York, England), a vibrating fork transmitter (akin to a SOLARTRON® Visconic industrial viscosity transmitter, available from Mobrey Inc. of Houston, Tex.), or a vibrational-read viscometer. Of course, the actual viscosity sensor 24 for use in the engine 20 of FIG. 3 should be robust enough to function in an engine environment and sized accordingly to fit in a desired size and space.

Many types of temperatures sensors 28 that are capable of being electronically coupled to the processor may be utilized individually or in combination in the exemplary embodiments. They are of many types and can have all sorts of shapes. For example, one general purpose temperature sensor 28 according to one exemplary embodiment may be a small cylinder (for a platinum temperature detector, a.k.a. Pt RTD). Another type of general purpose temperature sensor 28 according to another exemplary embodiment may be a welding junction of two wires made of dissimilar metals (for a thermocouple). Still another general purpose temperature sensor 28 that may be used is a small temperature dependent resistor deposited on a flat ceramic substrate, otherwise known as a thermistor. Of course, the actual temperature sensor 28 for use in the engine 20 of FIG. 3 should be robust enough to function in an engine environment and sized accordingly to fit in a desired size and space.

In still another exemplary embodiment, the temperature sensor 28 and viscosity sensor 24 may be combined into an on-line viscometer with integrated temperature sensor, in a similar fashion to the VISCOLITE 1100X1 on-line viscometer disclosed above, which includes a 100 ohm Pt RTD built into its body.

The processor 26 is equipped with an algorithm that is capable of receiving electronic input from the sensors 24, 28 and determining either a size of hysteresis, or a sign of hysteresis, or both a size and sign of hysteresis, at predetermined time intervals as a function of the measured viscosity and temperature of the oil 22. The processor 26 may also include an algorithm to determine an absolute amplitude and/or a viscosity amplitude of the engine oil 22.

The processor 26 may therefore compute the level of oil degradation and detect the formation of sludge precursors at any given point in time as a function of the size of hysteresis or the sign of hysteresis, or both a size and sign of hysteresis, for a given thermal cycle. In another exemplary embodiment, the processor may also factor in the viscosity value and the absolute amplitude of the hysteresis of the engine oil during a particular heating-cooling cycle. When the level of oil degradation in the engine oil 22 reaches a predetermined value, as determined by the measured viscosity and temperature, or the onset of sludge formation is detected through a change in the sign of the hysteresis, a notification may be sent from the processor 26 to an operator.

When the engine 22 is coupled within an automobile 40, as shown in FIG. 3, the notification may be sent from the processor 26 to a check engine light 50, which may be located in the passenger compartment 52 of the automobile 40.

In one exemplary embodiment, the processor 26 may be coupled to the engine 20 in such a way as it is able to detect combustion events. When these combustion events begin, such as when the engine is first turned on, the processor 26 will read the viscosities as the oil temperature increases between two predetermined temperature values, also known as a predetermined minimum temperature value and a predetermined maximum temperature value. For example, as shown in FIGS. 1A-1B and 2A-2B above, the temperatures may be between about 20 and 105 degrees Celsius as thus corresponds approximately with the heating viscosity curve 12 of FIGS. 1A and 2A. When the engine 20 is subsequently turned off, the processor 26 takes a series of viscosities measurements as the engine oil cools down between the two predetermined temperature values (i.e. similar to the cooling viscosity curve 14 of FIGS. 1A and 2A). This completes one heating-cooling cycle 10 in a manner similar to that described above with respect to FIGS. 1A-1B and 2A-2B.

The processor 26 may then be able to determine the sign of hysteresis and calculate the size of hysteresis, for that particular thermal cycle.

Thus, in one exemplary embodiment, wherein the processor 26 may determine a size of hysteresis has reached a predetermined value in any one thermal cycle, indicating that the rate of oxidation and onset of sludge precursors formation for the engine oil has reached a predetermined critical value, the processor 26 may then send a signal to the operator. As in FIG. 3, this may be done by sending a signal to illuminate a check engine light 50.

Similarly, in another exemplary embodiment, wherein the processor 26 may determine that the sign of hysteresis has changed from negative to positive, indicating the start of severe oil degradation and the onset of sludge formation for the engine oil, the processor 26 may send a signal to the operator. As in FIG. 3, this may be done by sending a signal to illuminate a check engine light 50.

In another related embodiment, the processor 26 may be configured to send a signal to the check engine light 50 when either the size of hysteresis has reached a predetermined value in a single thermal cycle or where the sign of hysteresis has changed in successive thermal cycles.

In yet another related embodiment, the processor 26 may also be configured to factor in the viscosity value in addition to either the size of hysteresis or changing sign of hysteresis or both the size and changing sign of hysteresis, in determining when to notify the operator. Similarly, the processor 26 may also be configured to factor in the relative viscosity change over numerous heating-cooling cycles, in addition to either the size of hysteresis or changing sign of hysteresis or both the size and changing sign of hysteresis, in determining when to notify the operator. Also, the processor 26 may be configured to factor in the viscosity value and the relative viscosity change over numerous heating-cooling cycles, in addition to the either the size of hysteresis, the relative hysteresis value or changing sign of hysteresis or both the size and changing sign of hysteresis.

The exemplary embodiments herein may provide a simple method for determining the onset of rapid oil degradation and sludge formation that is based on the breakdown of the engine oil 20 itself in real time, and not predictive indicators such as time or distance traveled (for automotive applications) or based merely on the number of combustion events. The method is robust in that it relies on internal consistency checks through the use of several criteria for establishing the extent of oil degradation. The method may provide increased engine durability, reduced warranty costs, and reduced oil change frequency.

The above description of embodiments of the invention is merely exemplary in nature and, thus, variations thereof are not to be regarded as a departure from the spirit and scope of the invention.

What is claimed is:

1. A method comprising:
providing an engine having a quantity of engine oil;
determining a size of viscosity hysteresis of said quantity of engine oil in a heating-cooling cycle as a function of a measured temperature of said quantity of engine oil; and
determining a state of engine oil degradation in said quantity of engine oil from said heating-cooling cycle as a function of the size of viscosity hysteresis for said heating-cooling cycle.

2. The method of claim 1, wherein the determining a size of hysteresis of said quantity of engine oil as a function of a measured temperature of said quantity of engine oil comprises:
heating said quantity of engine oil from a first predetermined temperature to a second predetermined temperature;
measuring a first set of viscosity values at one or more temperatures for said quantity of engine oil as said quantity of engine oil is heated between said first predetermined temperature and said second predetermined temperature;
subsequently cooling said quantity of engine oil from said second predetermined temperature to said first predetermined temperature;
measuring a second set of viscosity values for said quantity of engine oil at one or more temperatures as said quantity of engine oil is cooled from said second predetermined temperature to said first predetermined temperature;
determining a size of viscosity hysteresis from the absolute value of the difference between said first set of viscosity values and said second set of viscosity values; and
notifying an operator of said engine when said size of hysteresis reaches a predetermined minimum level.

3. The method of claim 1, further comprising:
coupling a processor to said engine;
coupling at least one temperature sensor to said engine, said at least one temperature sensor being constructed and arranged to measure a temperature of said quantity of engine oil;
electronically coupling said at least one temperature sensor to said processor;
coupling at least one viscosity sensor to said engine, said at least one viscosity sensor being constructed and arranged to measure a viscosity of said quantity of engine oil; and
electronically coupling said at least one viscosity sensor to said processor.

4. The method of claim 2, wherein notifying an operator comprises:
coupling a processor to said engine;
coupling a check engine light to said processor; and
actuating said check engine light to notify said operator of said engine when said size of hysteresis reaches a predetermined level.

5. The method of claim 2 further comprising:
reheating said quantity of engine oil from said first predetermined temperature to said second predetermined temperature;
measuring a third set of viscosity values at one or more temperatures for said quantity of engine oil as said quantity of engine oil is reheated from said first predetermined temperature to said second predetermined temperature;
subsequently cooling said quantity of engine oil from said second predetermined temperature to said first predetermined temperature;
measuring a fourth set of viscosity values at one or more temperatures for said quantity of engine oil as said quantity of engine oil is subsequently cooled from said second predetermined temperature to said first predetermined temperature;
determining a first sign of hysteresis by comparing said first set of viscosity values to said second set of viscosity values;
determining a second sign of hysteresis by comparing said third set of viscosity values to said fourth set of viscosity values;
comparing said first sign of hysteresis to said second sign of hysteresis; and
notifying said operator when said first sign of hysteresis is different than said second sign of hysteresis.

6. The method of claim 5, wherein notifying said operator when said first sign of hysteresis is different than said second sign of hysteresis comprises:
notifying said operator when said first sign of hysteresis is different than said second sign of hysteresis and when said size of hysteresis reaches a predetermined minimum level.

7. The method of claim 2 further comprising:
reheating said quantity of engine oil from said first predetermined temperature to said second predetermined temperature;
measuring a third set of viscosity values for said quantity of engine oil as said quantity of engine oil is reheated from said first predetermined temperature to said second predetermined temperature;
subsequently cooling said quantity of engine oil from said second predetermined temperature to said first predetermined temperature;
measuring a fourth set of viscosity values for said quantity of engine oil as said quantity of engine oil is subsequently cooled from said second predetermined temperature to said first predetermined temperature; and
notifying the operator when said first set of viscosity values, said second set of viscosity values, said third set of viscosity values or said fourth set of viscosity values reaches a predetermined viscosity value or when said size of hysteresis reaches a predetermined level.

8. The method of claim 2 further comprising:
subsequently heating said quantity of engine oil from said first predetermined temperature to said second predetermined temperature;
measuring a third set of viscosity values at one or more temperatures for said quantity of engine oil as said quantity of engine oil is subsequently heated from said first predetermined temperature to said second predetermined temperature;
subsequently cooling said quantity of engine oil from said second predetermined temperature to said first predetermined temperature;
measuring a fourth set of viscosity values at one or more temperatures for said quantity of engine oil as said quantity of engine oil is subsequently cooled from said second predetermined temperature to said first predetermined temperature; and
notifying the operator when a relative viscosity change at a predetermined temperature or a selected set of predetermined temperatures, between said first set of viscosity values and said third set of viscosity values reaches a predetermined level or when a relative viscosity change between said second set of viscosity values and said fourth set of viscosity values reaches a predetermined level or when said size of hysteresis reaches a predetermined level.

9. The method of claim 5 further comprising:
notifying the operator when said first set of viscosity values, said second set of viscosity values, said third set of viscosity values or said fourth set of viscosity values reaches a predetermined viscosity amplitude or when said size of hysteresis reaches a predetermined level or when said first sign of hysteresis is different than said second sign of hysteresis.

10. The method of claim 5 further comprising:
notifying the operator when a relative viscosity change at a predetermined temperature or a set of predetermined temperatures between said first set of viscosity values and said third set of viscosity values reaches a predetermined level or when a relative viscosity change between said second viscosity and said fourth viscosity reaches a predetermined level or when said size of hysteresis reaches a predetermined level or when said first sign of hysteresis is different than said second sign of hysteresis.

11. The method of claim 1 further comprising:
determining a relative hysteresis value for said quantity of engine oil for a single thermal cycle; and
determining a state of engine oil degradation in said quantity of engine oil as a function of said determined relative hysteresis value.

12. A method comprising:
providing an engine having a quantity of engine oil;
determining a first sign of hysteresis of said quantity of engine oil in a first heating-cooling cycle of said quantity of engine oil;
determining a second sign of hysteresis of said quantity of engine oil in a subsequent heating-cooling cycle of said quantity of engine oil; and
determining a state of engine oil degradation for said quantity of engine oil by comparing said first sign of hysteresis to said second sign of hysteresis.

13. The method of claim 12, further comprising:
coupling a processor to said engine;
coupling at least one temperature sensor to said engine, said at least one temperature sensor being constructed and arranged to measure a temperature of said quantity of engine oil;
electronically coupling said at least one temperature sensor to said processor;
coupling at least one viscosity sensor to said engine, said at least one viscosity sensor capable of measuring a viscosity of said quantity of engine oil; and
electronically coupling said at least one viscosity sensor to said processor; and
notifying an operator of said engine when said first sign of hysteresis is different than said second sign of hysteresis.

14. The method of claim 13, wherein notifying an operator of said engine when said first sign of hysteresis is different than said second sign of hysteresis comprises:
coupling a check engine light to said processor; and
actuating said check engine light to notify said operator of said engine when said first sign of hysteresis is different than said second sign of hysteresis.

15. The method of claim 12, wherein the determining a first sign of hysteresis comprises:
heating said quantity of engine oil from a first predetermined temperature to a second predetermined temperature;
measuring a first viscosity of said quantity of engine oil at one or more temperatures as said quantity of engine oil is heated between said first predetermined temperature and said second predetermined temperature;
subsequently cooling said quantity of engine oil from said second predetermined temperature to said first predetermined temperature;
measuring a second viscosity of said quantity of engine oil at one or more temperatures as said quantity of engine oil is cooled from said second predetermined temperature to said first predetermined temperature; and
determining a first sign of hysteresis by comparing said first viscosity to said second viscosity.

16. The method of claim 15, wherein the determining a second sign of hysteresis comprises:
reheating said quantity of engine oil from said first predetermined temperature to said second predetermined temperature;
measuring a third viscosity of said quantity of engine oil as said quantity of engine oil is reheated from said first predetermined temperature to said second predetermined temperature;
subsequently cooling again said quantity of engine oil from said second predetermined temperature to said first predetermined temperature;
measuring a fourth viscosity of said quantity of engine oil at one or more temperatures as said quantity of engine oil is cooled from said second predetermined temperature to said first predetermined temperature; and
determining a second sign of hysteresis by comparing said third viscosity to said fourth viscosity.

17. The method of claim 16 further comprising:
notifying an operator when said first viscosity, said second viscosity, said third viscosity or said fourth viscosity reaches a predetermined viscosity amplitude or when said first sign of hysteresis is different than said second sign of hysteresis.

18. The method of claim 16 further comprising:
notifying an operator when a relative viscosity change between said first viscosity and said third viscosity reaches a predetermined level or when a relative viscosity change between said second viscosity and said fourth viscosity reaches a predetermined level or when said first sign of hysteresis is different than said second sign of hysteresis.

19. A method comprising:

providing an engine having a quantity of engine oil;

heating said quantity of engine oil from a first predetermined temperature to a second predetermined temperature;

measuring a first set of viscosity values at one or more temperatures for said quantity of engine oil as said quantity of engine oil is heated between said first predetermined temperature and said second predetermined temperature;

subsequently cooling said quantity of engine oil from said second predetermined temperature to said first predetermined temperature;

measuring a second set of viscosity values for said quantity of engine oil at one or more temperatures as said quantity of engine oil is cooled from said second predetermined temperature to said first predetermined temperature;

subsequently heating said quantity of engine oil from said first predetermined temperature to said second predetermined temperature;

measuring a third set of viscosity values at one or more temperatures for said quantity of engine oil as said quantity of engine oil is subsequently heated from said first predetermined temperature to said second predetermined temperature;

subsequently cooling said quantity of engine oil from said second predetermined temperature to said first predetermined temperature;

measuring a fourth set of viscosity values at one or more temperatures for said quantity of engine oil as said quantity of oil is subsequently cooled from said second predetermined temperature to said first predetermined temperature;

comparing said first set of viscosity values to said third set of viscosity values and comparing said second set of viscosity values to said fourth set of viscosity values at a predetermined temperature to determine a relative viscosity change in successive thermal cycles at said predetermined temperature; and determining a state of engine oil degradation in said quantity of engine oil in said successive thermal cycles as a function of said determined relative viscosity change.

20. The method of claim 19 further comprising:

notifying an operator of said engine when said determined relative viscosity change at said predetermined temperature reaches a predetermined minimum level.

* * * * *